United States Patent [19]

Wetzel et al.

[11] 4,454,128

[45] Jun. 12, 1984

[54] 6α-METHOXY-PENICILLINS

[75] Inventors: Bernd Wetzel; Wolfgang Eberlein; Günter Trummlitz; Eberhard Woitun; Roland Maier; Wolfang Reuter; Uwe Lechner; Hanns Goeth, all of Biberach, Fed. Rep. of Germany

[73] Assignee: Dr. Karl Thomae GmbH, Biberach an der Riss, Fed. Rep. of Germany

[21] Appl. No.: 410,007

[22] Filed: Aug. 20, 1982

[30] Foreign Application Priority Data

Sep. 2, 1981 [DE] Fed. Rep. of Germany ....... 3134776

[51] Int. Cl.³ ................ A61K 31/635; A61K 31/505; C07D 499/54
[52] U.S. Cl. ................. 424/229; 260/239.1; 424/251
[58] Field of Search .............. 424/229, 251; 260/239.1

[56] References Cited

U.S. PATENT DOCUMENTS 4,316,898 2/1982 Wetzel et al. ................. 424/246

Primary Examiner—Natalie Trousof
Assistant Examiner—Vera C. Clarke
Attorney, Agent, or Firm—Hammond & Littell, Weissenberger & Dippert

[57] ABSTRACT

Compounds of the formula

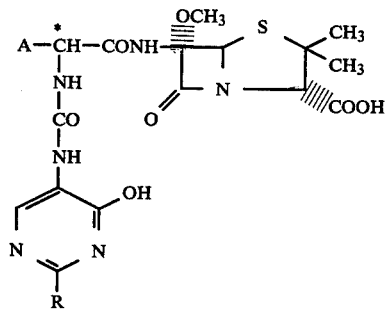

wherein
A is phenyl, p=hydroxy-phenyl, 2-thienyl or 3-thienyl; and
R represents substituents of various types;
and non-toxic, pharmacologically acceptable salts thereof formed with inorganic or organic bases. The compounds as well as their salts are useful as antibiotics.

7 Claims, No Drawings

6α-METHOXY-PENICILLINS

This invention relates to novel 6α-methoxy-penicillins and salts thereof, to methods of preparing these compounds, to pharmaceutical compositions containing them as active ingredients, and to methods of using them as antibiotics.

More particularly, the present invention relates to a novel class of penicillins represented by the formula

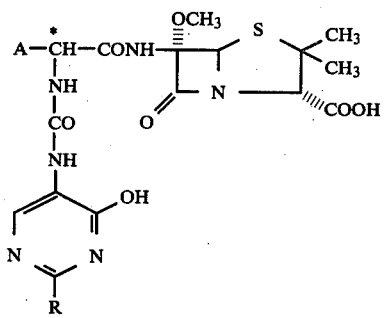

wherein

A is phenyl, p-hydroxy-phenyl, 2-thienyl or 3-thienyl; and

R is cyclopropyl, —NH—R$_1$,

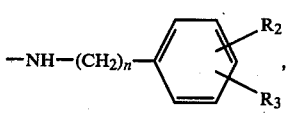

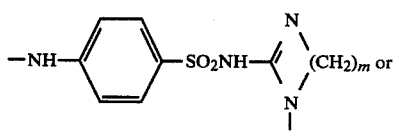

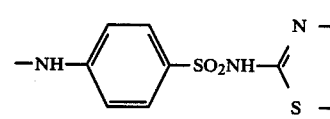

R$_1$ is straight or branched aliphatic hydrocarbyl of 1 to 4 carbon atoms; straight or branched aliphatic hydrocarbyl of 2 to 4 carbon atoms hydroxy-substituted in 2-, 3- or 4-position; cycloalkyl of 3 to 6 carbon atoms; hydroxy-(cycloalkyl of 3 to 6 carbon atoms; unsubstituted or monosubstituted 3-pyridyl, where the substituent is hydroxyl, methylsulfinyl, methylsulfonyl or aminosulfonyl; unsubstituted or monosubstituted 2-furylmethyl, where the substituent is hydroxyl, methylsulfinyl, methylsulfonyl or aminosulfonyl; unsubstituted or monosubstituted 2-thiazolylmethyl, where the substituent is hydroxyl, methylsulfinyl, methylsulfonyl or aminosulfonyl; unsubstituted or monosubstituted 2-thienylmethyl, where the substituent is hydroxyl, methylsulfinyl, methylsulfonyl or aminosulfonyl; unsubstituted or monosubstituted 3-imidazolylmethyl, where the substituent is hydroxyl, methylsulfinyl, methylsulfonyl or aminosulfonyl; or unsubstituted or monosubstituted 3-pyridylmethyl, where the substituent is hydroxyl, methylsulfinyl, methylsulfonyl or aminosulfonyl;

n is 0 or 1;

R$_2$ and R$_3$, which may be identical to or different from each other, are each hydrogen, hydroxyl, acetylamino, aminocarbonylamino, nitro, aminocarbonyl, cyano, methylsulfinyl, methylsulfonyl, aminosulfonyl, methylaminosulfonyl, aminocarbonyl-methyleneaminosulfonyl, 2'-hydroxy-ethyl-aminosulfonyl, cyano-aminosulfonyl, aminocarbonyl-aminosulfonyl, acetyl-aminosulfonyl, methylsulfonyl-aminosulfonyl or acetyl-hydrazinosulfonyl; and m is 2, 3 or 4;

and non-toxic, pharmacologically acceptable salts thereof formed with inorganic or organic bases.

Preferred specific embodiments of substituent R are the following:

p-Aminosulfonylanilino, p-methylsulfinylanilino, p-methylsulfonylanilino, m-hydroxy-p-aminosulfonylanilino, p-aminocarbonylmethyleneamino-sulfonylanilino, p-(4',5'-dihydro-imidazol-2'-yl)-aminosulfonylanilino, p-(3',4',5',6'-tetrahydro-pyrimidin-2'-yl)-aminosulfonylanilino, p-(4',5',6',7'-tetrahydro-1,3-diazepin-2'-yl)-aminosulfonylanilino, p-(4',5'-dihydro-thiazol-2'-yl)-aminosulfonylanilino, p-hydroxybenzylamino, p-aminosulfonylbenzylamino, isopropylamino, 4'-hydroxy-cyclohexylamino, 5'-aminosulfonyl-2'-thienylmethylamino, 2'-furylmethylamino, 3'-pyridylmethylamino or 4'-hydroxy-3'-pyridylamino.

The penicillins of the formula I may occur in two tautomeric forms, namely the lactim and the lactam form:

Which of the two forms I or I' predominates depends particularly on the solvent used in their preparation and the nature of the substituent R.

It should be understood that the compounds of the form I specified hereinabove always include both tautomers.

The compounds of the formula I may be present in the two possible R- and S-configurations with regard to the chiral centre C, but may also be present as a mixture of these two configurations. Compounds of the D=R-configuration are particularly preferred.

The compounds of the formula I may be prepared by the following method:

By reacting a compound of the formula

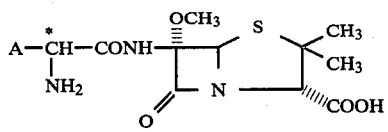 (II)

wherein A has the meanings previously defined, with a pyrimidine derivative of the formula

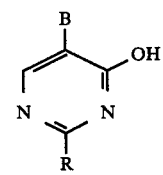 (III)

or

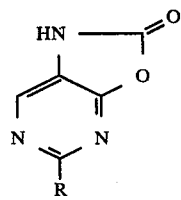 (IIIa)

optionally prepared in the reaction mixture, wherein R has the meanings previously defined and B represents the group —NCO or a reactive derivative of the group —NHCOOH, such as, for example, the groups —NHCOCl, —NHCOBr or

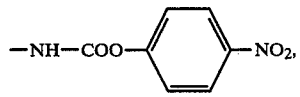

the group —NHCOCl being particularly preferred. It is also possible to use mixtures of pyrimidine derivatives of the formula III wherein B has partly one and partly the other of the above meanings, for example represents the groups —NCO and —NHCOCl together at the same time.

The starting compounds of the formula II may be used in the form of their inorganic or organic salts, for instance as the triethylammonium salt or sodium salt. The reaction may then be effected in any desired mixtures of water and water-miscible organic solvents, for instance ketones such as acetone; cyclic ethers such as tetrahydrofuran or dioxane; nitriles such as acetonitrile; formamides such as dimethylformamide; dimethylsulfoxide; or alcohols such as isopropanol; or in hexametapol. The pH of the reaction mixture is kept within a range of about 2.0 to 9.0, preferably between pH 6.5 and 8.0, by the addition of bases or by using buffer solutions. However, it is also possible to perform the reaction in anhydrous organic solvents, for example halogenated hydrocarbons such as chloroform or methylene chloride, in the presence of a base, preferably triethylamine, diethylamine or N-ethyl-piperidine. Moreover, the reaction may be carried out in a mixture of water and a water-immiscible solvent, for example ethers such as diethyl ether; halogenated hydrocarbons such as chloroform or methylene chloride; carbon disulfide; ketones such as isobutyl methyl ketone; esters such as ethyl acetate; or aromatic solvents such as benzene, advantageously while vigorously stirring and keeping the pH value within the range from about 2.0 to 9.0, preferably between 6.5 and 8.0, by the addition of a base or using buffer solutions. However, the reaction may also be carried out in water only, in the presence of an organic or inorganic base or with the addition of buffers.

If the starting compounds are the silyl derivatives of the compounds of the formula II (for instance mono- or di-trimethylsilyl derivatives) and if they are reacted with compounds of the formula III or IIIa, it is generally advantageous to work in anhydrous solvents free from hydroxyl groups, for instance in halogenated hydrocarbons such as methylene chloride or chloroform, benzene, tetrahydrofuran, acetone or dimethylformamide, etc. The addition of bases is not essential but may be advantageous in certain cases so as to improve the yield and purity of the products. Advantageously, the bases which are optionally added are tertiary aliphatic or aromatic amines such as pyridine or triethylamine, or secondary amines which are difficult to acylate on account of steric hindrance, such as dicyclohexylamine.

Instead of silyl esters it is also possible to use any other carboxyl derivatives of the 6α-methoxy-penicillin derivatives of the formula II which are known in the art of the preparation of semi-synthetic penicillins. Typical examples are the trityl, p-nitrobenzyl and phenacyl esters or the β,β,β-trichloroethyl esters. After the reaction, these derivatives may be converted into the penicillins of the present invention, using known methods. The quantity of base to be used is determined, for example, by the need to maintain a specific pH value. Where measurement and adjustment of the pH is not carried out or is not possible or practical, owing to the lack of sufficient water in the diluent, preferably 1.0 to 2.0 mol-equivalents of base are added when non-silylated compounds of the formula II are used. When the silylated compounds are used, preferably up to one mol-equivalent of base is used.

As bases, it is theoretically possible to use all the organic and inorganic bases conventionally used in organic chemistry, such as alkali metal and alkaline earth metal hydroxides, alkaline earth metal oxides, alkali metal and alkaline earth metal carbonates and bicarbonates, ammonia, primary, secondary and tertiary aliphatic and aromatic amines and heterocyclic bases. Examples are sodium, potassium and calcium hydroxide, calcium oxide, sodium and potassium carbonate, sodium and potassium bicarbonate, ethylamine, methylethylamine, triethylamine, hydroxyethylamine, aniline, pyridine and piperidine. However, when the silylated starting materials are used, the above restrictions regarding the types of bases should be observed.

As buffer systems it is possible to use any conventional buffer mixtures, for example phosphate buffers, citrate buffers and tris(hydroxymethyl)amino-methane buffers.

The reaction temperature may be varied within a fairly wide range. Generally, the reaction is performed between about −20° and +50° C., preferably between 0° and +20° C.

The reaction partners of the formula II and III or IIIa may be brought to reaction with each other in equimolar quantities from the start. In individual cases, however, it may be advantageous to use one of the two reaction partners in excess, so as to aid purification of the end product or increase the yield.

After the reaction is complete, the reaction mixture is worked up by using the methods conventionally used with β-lactam antibiotics; the same applies to the isolation and purification of the end products, for example the liberation of the acid from its salts and the conversion of the free acid into other salts by means of inorganic or organic bases. For preparing the potassium or sodium salts it has proved particularly useful to precipitate these salts from an alcoholic-ethereal solution of the free acid, by adding potassium or sodium 2-ethylhexanoate or by adding equimolar amounts of potassium or sodium bicarbonate, and then freeze-drying the mixture.

The 6α-methoxy-penicillin derivatives of the formula II used as starting compounds are known from the literature, or may be prepared in analogy to methods known from the literature (cf., for example, Bentley et al., J. Chem. Soc. 1979, p. 2455; U.S. Pat. No. 4,044,000; or U.S. Pat. No. 4,035,359).

The starting compounds of the formula III or IIIa may be obtained, for example, by reacting a corresponding 5-aminopyrimidine of the formula

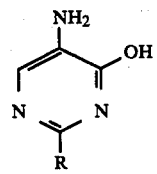

(IV)

wherein R has the meanings previously defined, with phosgene. This reaction is preferably carried out in a solvent which does not contain hydroxyl groups, such as tetrahydrofuran, methylene chloride, chloroform, dimethoxyethane or hexametapol, at temperatures between −40° C. and +60° C., preferably between −10° and +20° C. It is advisable to bind the resulting hydrogen chloride with equimolar quantities of an inert organic base such as triethylamine or pyridine. Pyridine in excess may also be used as the solvent. If the respective aminopyrimidines of the formula IV do not dissolve readily in one of the above-mentioned solvents, phosgenation may also be effected in the heterogeneous phase. Moreover, the aminopyrimidines of the formula IV may be converted by treating them with a silylating agent such as hexamethyldisilazane, trimethylchlorosilane/triethylamine or trimethylsilyldiethylamine into an aminopyrimidine which is generally very readily soluble in the above-mentioned solvents and which is mono- or polysilylated, depending on the exchangeable hydrogen atoms which are present, and which then reacts with phosgene to form the corresponding compound of the formula III or IIIa. Depending on the type of solvent, the temperature, and the quantity and nature of the base which is used, either the corresponding isocyanate or carbamic acid halide is predominantly formed or a mixture of these two compounds is formed.

The starting compounds of the formula III or IIIa obtained by phosgenation or the mixtures thereof are generally readily soluble in the above-mentioned solvents and, after removal of the excess phosgene, can be reacted directly, without further purification, with the corresponding penicillin derivatives of the formula II. The synthesis of the aminopyrimidines of the formula IV is described in U.S. Pat. No. 4,241,056.

The following Table lists some typical, particularly effective penicillins according to this invention.

| A | R |
|---|---|
| Phenyl- | p-Sulfamoylanilino- |
| p-Hydroxyphenyl- | p-Sulfamoylanilino- |
| 2-Thienyl- | p-Sulfamoylanilino- |
| 3-Thienyl- | p-Sulfamoylanilino- |
| Phenyl- | m-Hydroxy-p-sulfamoylanilino- |
| p-Hydroxyphenyl- | m-Hydroxy-p-sulfamoylanilino- |
| p-Hydroxyphenyl- | p-Methylsulfinylanilino- |
| Phenyl- | p-Methylsulfonylanilino- |
| p-Hydroxyphenyl- | p-Methylsulfonylanilino- |
| p-Hydroxyphenyl- | 4'-Hydroxycyclohexylamino- |
| p-Hydroxyphenyl- | p-Hydroxybenzylamino- |
| Phenyl- | 5'-Sulfamoyl-2'-thienylmethylamino- |
| p-Hydroxyphenyl- | 5'-Sulfamoyl-2'-thienylmethylamino- |
| 2-Thienyl- | 5'-Sulfamoyl-2'-thienylmethylamino- |
| Phenyl- | 2'-Furylmethylamino- |
| p-Hydroxyphenyl- | 2'-Furylmethylamino- |
| Phenyl- | 3'-Pyridylmethylamino- |
| p-Hydroxyphenyl- | 3'-Pyridylmethylamino- |
| p-Hydroxyphenyl- | 4'-Hydroxy-3'-pyridylamino- |
| Phenyl- | 4'-Hydroxy-3'-pyridylamino- |
| p-Hydroxyphenyl- | p-Aminocarbonylmethyl-sulfamoylanilino- |
| p-Hydroxyphenyl- | p-(4',5'-Dihydro-imidazol-2'-yl)-sulfamoylanilino- |
| p-Hydroxyphenyl- | p-(3',4',5',6'-Tetrahydro-pyrimidin-2'-yl)-sulfamoylanilino- |
| p-Hydroxyphenyl- | p-(4',5',6',7-Tetrahydro-1,3-diazepin-2'-yl)-sulfamoylanilino- |
| p-Hydroxyphenyl- | p-(4',5'-Dihydro-thiazol-2'-yl)-sulfamoylanilino- |

The following examples illustrate the present invention and will enable others skilled in the art to understand it more completely. It should be understood, however, that the invention is not limited solely to the particular examples given below.

EXAMPLE 1

6β-{D-α-[3-(4-hydroxy-2-p-sulfamoylanilino-5-pyrimidinyl)-ureido]-benzylamido}-6α-methoxy-penicillanic acid sodium salt 1.9 gm (0.005 mol) of 6α-methoxy-ampicillin monohydrate were suspended in 100 ml of 80% aqueous tetrahydrofuran and put into solution with triethylamine, while cooling with ice. At 5° C., 1.55 gm of solid 1-hydro-5-(4-sulfanilamido)-oxazolo-[5,4-d]-pyrimidin-2-one (0.005 mol) were added in batches. The pH was kept at 7.5 with triethylamine. The mixture was stirred at room temperature for one hour, 30 ml of water were added, and the tetrahydrofuran was removed in vacuo at 25° C. The aqueous solution was washed twice with ethyl acetate at pH 7.0 and then adjusted to pH 2.8 with 1N hydrochloric acid, while cooling with ice. The precipitate was suction-filtered and dried. The product was put into solution with an equimolar quantity of sodium 2-ethylhexanoate in 30 ml of methanol, and the sodium salt was immediately precipitated by the addition of 200 ml of diethyl ether.

Yield: 1.85 gm of sodium salt (52%).
IR-Spectrum: 1765, 1660, 1600, 1540 cm$^{-1}$.
NMR-Spectrum (DMSO, CD$_3$OD) Signals at ppm: 1.0+1.25 (2s,6H), 3.45 (s, 3H), 3.9 (s, 1H), 5.35 (s, 1H), 5.5 (1, 1H), 7.2–7.6 (m, 5H), 7.8 (q, 4H), 8.3 (s, 1H).

EXAMPLE 2

6β-{D-α-[3-(4-Hydroxy-2-(5'-sulfamoyl-2'-thienylmethylamino)-5-pyrimidinyl)-ureido]-benzylamido}-6α-methoxypenicillanic acid sodium salt 900 mg of 5-amino-4-hydroxy-2-(5'-sulfamoyl-2'-thienylmethylamino)-pyrimidine (0.003 mol) were suspended in 50 ml of anhydrous tetrahydrofuran and, after the addition of 5 ml of trimethylsilyldiethylamine, the mixture was stirred at room temperature for 2½ hours.

It was then evaporated to dryness at 30° C. and dried for 30 minutes in a high vacuum. The residue was taken up in 50 ml of anhydrous tetrahydrofuran and, at 0° to 5° C., the solution was added dropwise to 3.75 ml of a phosgene solution containing 20 gm of phosgene in 250 ml of anhydrous tetrahydrofuran. The mixture was stirred at room temperature for 30 minutes and then evaporated down to a volume of about 40 ml at a temperature of not more than 30° C. (solution I).

1.145 gm (3.1 mmols) of 6α-methoxy-ampicillin monohydrate were suspended in 80 ml of 80% aqueous tetrahydrofuran and put into solution by adjusting the pH value to 8.3 with triethylamine. Solution I was added dropwise at 5° to 10° C., and the pH was maintained at 7.5 by the addition of triethylamine. The mixture was stirred for one hour at room temperature, then 30 ml of water were added, and the tetrahydrofuran was removed in vacuo at 30° C. The residual aqueous solution was adjusted to pH 2.7 with 2N hydrochloric acid, while being cooled, and the precipitate was suction-filtered off, washed with water and dried. The product was suspended in methanol and sodium 2-ethylhexanoate was added. After the addition of diethyl ether, 1.03 gm (48% of theory) of the title compound were obtained in the form of a colorless powder.

IR-Spectrum: 1765, 1660 cm$^{-1}$.
NMR-Spectrum DMSO, CD$_3$OD) Signals at ppm: 1.0+1.25 (2s, 6H), 3.46 (s, 3H), 3.9 (s, 1H), 4.65 (s, 2H), 5.4 (s, 1H), 5.55 (s, 1H), 7.05 (d, 1H), 7.45 (m, 5+1H), 8.15 (s, 1H).

The sodium salts of the compounds of the formula I listed in the following table were prepared analogously.

| Example No. | A | R | % Yield | IR-Spectrum cm$^{-1}$ | NMR-Spectrum (CMSO, CD$_3$OD) Signals at ppm |
|---|---|---|---|---|---|
| 3 | HO—⟨⟩— | —NH—⟨⟩—SO$_2$NH$_2$ | 57.5 | 1765, 1655 | 1.05 + 1.25 (2s, 6H), 3,4 (s, 3H), 3.9 (s, 1H), 5.35 (2s, 2H), 6.7 (d, 2H), 7.3 (d, 2H), 7.75 (q, 4H), 8.3 (s, 1H). |
| 4 | HO—⟨⟩— | —NH—CH$_2$—⟨⟩—SO$_2$NH$_2$ | 44 | 1765, 1660, 1610 | 1.0 + 1.2 (2s, 6H), 3.4 (s, 3H), 3.85 (s, 1H), 4.60 (s, 2H), 5.3 (s, 1H), 5.45 (s, 1H), 6.7 (d, 2H), 7.05 (d, 2H), 7.25 (d, 2H), 7.45 (d, 2H), 8.05 (s, 1H). |
| 5 | ⟨⟩— | ▷ (cyclopropyl) | 61.5 | 1765, 1655 | 0.95 (m, 4H), 1.0 + 1.3 (2s, 6H), 1.85 (m, 1H), 3.4 (s, 3H), 3.9 (s, 1H), 5.35 (2s, 2H), 7.5 (m, 5H), 8.35 (s, 1H). |
| 6 | ⟨⟩— | —NH—⟨⟩—SO$_2$CH$_3$ | 50 | 1765, 1660 | 1.0 + 1.3 (2s, 6H), 3.1 (s, 3H), 3,4 (s, 3H), 3.9 (s, 1H), 5.3 (s, 1H), 5.55 (s, 1H), 7.2–7.6 (m, 5H), 7.9 (q, 4H), 8.3 (s, 1H). |
| 7 | ⟨⟩— | —NH—⟨⟩—OH | 39 | 1765, 1660 | 1.0 + 1.3 (2s, 6H), 3.4 (s, 3H), 3.85 (s, 1H), 5.3 (2s, 2H), 6.9 (d, 2H), 7.45 (m, 7H), 8.10 (s, 1H). |
| 8 | ⟨⟩— | —NHCH$_2$—(pyridyl) | 61.5 | 1765, 1660, 1605 | 1.0 + 1.3 (2s, 6H), 3.4 (s, 3H), 3.90 (s, 1H), 4.30 (s, 2H), 5.35 (s, 1H), 5.5 (s, 1H), 7.25 (m, 1H), 7.45 (m, 5H), 7.7 (m, 1H), 8.1 (s, 1H), 8.45 (m, 2H). |
| 9 | ⟨⟩— | —NH—⟨⟩(OH)—SO$_2$NH$_2$ | 53 | 1765, 1660, 1610 | 0.95 + 1.25 (2s, 6H), 3.4 (s, 3H), 3.85 (s, 1H), 5.3 (s, 1H), 5.5 (s, 1H), 7.0 (m, 1H), 7.2–7.7 (m, 7H), 8.3 (s, 1H). |
| 10 | HO—⟨⟩— | —NHCH$_2$—(furyl, O) | 55 | 1765, 1655 | 1.0 + 1.2 (2s, 6H), 3.4 (s, 3H), 3.8 (s, 1H), 4.35 (s, 2H), 5.25 (2s, 1H), 6.25 (m, 2H), 6.65 (d, 2H), 7.2 (d, 2H), 7.45 (m, 1H), 8.0 (s, 1H). |
| 11 | ⟨⟩— | —NHCH$_2$—(furyl, O) | 58.5 | 1765, 1655 | 1.0 + 1.3 (2s, 6H), 3.4 (s, 3H), 3.90 (s, 1H), 4.40 (s, 2H), 5.35 (s, 1H), 5.5 (s, 1H), 6.3 (m, 2H), 7.2–7.6 (m, 5 + 1H), 8.05 (s, 1H). |
| 12 | HO—⟨⟩— | —NH—⟨⟩(OH)—SO$_2$NH$_2$ | 69 | 1765, 1655 | 1.05 + 1.3 (2s, 6H), 3.4 (s, 3H), 3.85 (s, 1H), 5.35 (2s, 2H), 6.7 (d, 2H), 7.0–7.6 (m, 4H), 7.7 (s, 1H), 8.3 (s, 1H). |

| Example No. | A | R | % Yield | IR-Spectrum cm$^{-1}$ | NMR-Spectrum (CMSO, CD$_3$OD) Signals at ppm |
|---|---|---|---|---|---|
| 13 | HO–⟨⟩– | –NH–⟨⟩–SO$_2$CH$_3$ | 47 | 1765, 1655 | 1.0 + 1.25 (2s, 6H), 3.1 (s, 3H), 3.4 (s, 3H), 3.85 (s, 1H), 5.35 (2s, 2H), 6.7 (d, 2H), 7.3 (d, 2H), 7.7 (d, 2H), 8.0 (d, 2H), 8.3 (s, 1H). |
| 14 | HO–⟨⟩– | –NHCH$_2$–(thiophene)–SO$_2$NH$_2$ | 64 | 1765, 1660 | 1.0 + 1.25 (2s, 6H), 3.4 (s, 3H), 3.85 (s, 1H), 4.6 (s, 2H), 5.3 (2s, 2H), 6.65 (d, 2H), 6.9 (d, 1H), 7.25 (d + d, 1 + 2H), 8.0 (s, 1H). |
| 15 | HO–⟨⟩– | –NH–(pyridine)–OH | 59 | 1765, 1655 | 1.0 + 1.3 (2s, 6H), 3.45 (s, 3H), 3.85 (s, 1H), 5.35 (2s, 2H), 6.35 (d, 1H), 6.7 (d, 2H), 7.3 (d, 2H), 7.5 (dd, 1H), 7.9 (d, 1H), 8.15 (s, 1H). |
| 16 | HO–⟨⟩– | –NH–(cyclohexyl)–OH | 47 | 1765, 1655 | 1.0 (s, 3H), 1.2 (m, 4H), 1.25 (s, 3H), 1.85 (m, 2H), 3.4 (s, 3H), 3.42 (m, 1H), 3.55 (m, 1H), 3.85 (s, 1H), 5.32 (2s, 2H), 6.7 (d, 2H), 7.3 (d, 2H), 8.0 (s, 1H). |
| 17 | HO–⟨⟩– | –NHC$_3$H$_7$ | 72 | 1765, 1660 | 0.85 (t, 3H), 1.0 + 1.3 (2s, 6H), 1.5 (q, 2H), 3.4 (s, 3H), 3.9 (s, 1H), 5.35 (2s, 2H), 6.7 (d, 2H), 7.3 (d, 2H), 8.0 (s, 1H). |
| 18 | HO–⟨⟩– | –cyclopropyl | 86 | 1765, 1660 | 0.95 (m, 4H), 1.0 + 1.3 (2s, 6H), 1.85 (m, 1H), 3.4 (s, 3H), 3.9 (s, 1H), 5.3 (2s, 2H), 6.7 (d, 2H), 7.3 (d, 2H) 8.35 (s, 1H). |
| 19 | HO–⟨⟩– | –NH–⟨⟩–SO$_2$NH–(imidazoline) | 45 | 1765, 1660 | 1.05 + 1.3 (2s, 6H), 3.15 (m, 4H), 3.4 (s, 3H), 3.85 (s, 1H), 5.3 (2s, 2H), 6.7 (d, 2H), 7.3 (d, 2H), 7.6 (d, 2H), 7.85 (d, 2H), 8.25 (s, 1H). |
| 20 | HO–⟨⟩– | –NH–⟨⟩–SO$_2$NH–(tetrahydropyrimidine) | 58 | 1765, 1655 | 1.05 + 1.3 (2s, 6H), 1.8 (m, 2H), 3.15 (m, 4H), 3.4 (s, 3H), 3.85 (s, 1H), 5.35 (2s, 2H), 6.7 (d, 2H), 7.3 (d, 2H), 7.6 (d, 2H), 7.85 (d, 2H), 8.25 (s, 1H). |
| 21 | HO–⟨⟩– | –NH–⟨⟩–SO$_2$NH–(diazepine) | 61 | 1765, 1660 | 1.0 + 1.3 (2s, 6H), 1.55 (m, 4H), 3.05 (m, 4H), 3.4 (s, 3H), 3.9 (s, 1H), 5.35 (2s, 2H), 6.75 (d, 2H), 7.35 (d, 2H), 7.65 (d, 2H), 7.9 (d, 2H), 8.35 (s, 1H). |
| 22 | HO–⟨⟩– | –NH–⟨⟩–SO$_2$NH–(thiazoline) | 70 | 1765, 1660 | 1.05 + 1.3 (2s, 6H), 2.5 (m, 2H), 3.2 (m, 2H), 3.4 (s, 3H), 3.9 (s, 1H), 5.35 (2s, 2H), 6.7 (d, 2H), 7.3 (d, 2H), 7.6 (d, 2H), 7.9 (d, 2H), 8.25 (s, 1H). |

Whereas 7α-methoxy-cephalosporin derivatives have achieved great importance in chemotherapy in recent years, it has heretofore been almost impossible to synthesize 6α-methoxy-penicillins which exhibit high β-lactamase stability as well as good antibacterial activity. 6α-Methoxy-penicillins of this kind are described, for example, in European Pat. Nos. 0,029,871 and 0,015,690 and in German Offenlegungsschrift No. 2,732,104. The 6-methoxy derivative of ticarcillin of the formula

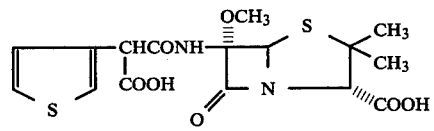

(Temocillin) has become known as a development substance [see, for example, J. Antimicrobial Agents and Chemotherapy 20, 38–46 (1981)].

The penicillin derivatives represented by formula I above exhibit an excellent anti-bacterial action, particularly against gram-negative bacteria, such as E. coli, Kl.

*pneumoniae, E. cloacae, Proteus species, Serratia marcescens* and also types of Pseudomonas, and this activity is clearly superior to that of Temocillin, both in vitro and in vivo.

In addition, they have excellent stability with respect to various β-lactamases and are thus effective against β-lactamase-carrying bacteria.

Moreover, the compounds of the present invention are well tolerated and can therefore be used for the prophylaxis and chemotherapy of local and systemic infections in human and veterinary medicine. Examples of diseases which can be prevented or cured with the compounds of this invention include diseases of the respiratory tract, the pharyngeal cavity and the urinary tract; the compounds are particularly effective against pharyngitis, pneumonia, peritonitis, pyelonephritis, otitis, cystitis, endocarditis, bronchitis, arthritis and general systemic infections.

As already explained, this is made possible by the fact that the compounds of general formula I are extremely effective both in vitro and in vivo against harmful microorganisms, particularly gram-positive and gram-negative bacteria and microorganisms resembling bacteria, and they are distinguished particularly by a broad range of activity.

These penicillin derivatives may be used, for example, to treat and/or prevent local and/or systemic diseases caused by the following pathogens or by mixtures of the following pathogens:

Micrococcaceae, such as Staphylococci;
Lactobacteriaceae, such as Streptococci;
Neisseriaceae, such as Neisseriae;
Corynebacteriaceae, such as Coryne bacteria;
Enterobacteriaceae, such as Escherichiae bacteria of the Coli group;
Klebsiella bacteria, e.g. K. pneumonia;
Proteae bacteria of the Proteus group, e.g., *Proteus vulgaris*;
Salmonella bacteria, e.g. S. typhimurium;
Shigella bacteria, e.g. *Shigella dysenteriae*;
Pseudomonas bacteria, e.g. *Pseudomonas aeruginosa*;
Aeromonas bacteria, e.g. *Aeromonas lique faciens*;
Spirillaceae, such as Vibrio bacteria, e.g., *Vibrio cholerae*;
Parvobacteriaceae or Brucellaceae, such as Pasteurella bacteria;
Brucella bacteria, e.g. *Brucella abortus*;
Haemophilus bacteria, e.g. *Haemophilus influenzae*;
Bordetella bacteria, e.g. *Bordetella pertussis*;
Moraxella bacteria, e.g. *Moraxella lacunata*;
Bacterioidaceae, such as Bacteroides bacteria;
Fusiforme bacteria, e.g. *Fusobacterium fusiforme*;
Sphaerophorus bacteria, e.g. *Sphaerophorus necrophorus*;
Bacillaceae, such as aerobic spore formers, e.g. *Bacillus anthracis*;
Anaerobic spore-forming Chlostridiae, e.g. *Chlostridium perfringens*;
Spirochaetaceae, such as Borrelia bacteria;
Treponema bacteria, e.g. *Treponema pallidum*;
Leptospira bacteria, such as *Leptospira interrogans*.

The above list of pathogens is purely by way of example and is in no way restrictive.

The activity of the 6α-methoxy-penicillins according to the invention can be demonstrated by way of example by the following tests:

1. Tests in vitro

For the tests, the method of the series dilution test in the microtiter system was used. The substances were tested for bacteriostasis in a liquid medium. The bacteriostatic activity was tested at the following concentration: 128; 64; 32; 16; 8; 4; 2; 1; 0.5; 0.25; 0.12; 0.06 μg/ml.

A nutrient medium having the following composition was used: 10 gm of peptone, 8 gm of meat extract oxoid, 3 gm of sodium chloride, 2 gm of sec. sodium phosphate are made up to 100 ml with distilled water (pH 7.2 to 7.4). The age of the primary cultures was about 20 hours.

The bacterial suspension was adjusted, using the photometer (according to "Eppendorf") (test tube diameter 14 mm, filter 546 nm) by reference to the turbidity of a barium sulfate comparison suspension which was produced by a barium sulfate suspension formed by the addition of 3.0 ml of 1% barium chloride solution to 97 ml of 1% sulfuric acid. After adjustment, Streptococcus aronson was diluted in the ratio 1:15 and the other test pathogens were diluted in the ratio 1:1500 with a common salt solution.

16 mg of the test substance were weighed in 10 ml measuring flasks and solvent was added up to the mark. Further dilutions in the series were made with distilled water or the solvent in question.

The depressions in the microtiter plates were filled with 0.2 ml of nutrient medium, 0.01 ml of the corresponding diluted substance and a drop of bacterial suspension (0.01 ml), and incubated for 18 to 20 hours at 37° C. A solvent check was carried out continuously at the same time.

The reading was taken macroscopically, and the respective limiting concentration (=the lower concentration still having bateriostatic activity) was determined.

The following were used as test organisms:
*Escherichia coli* ATCC 11 775, *Serratia marcescens* ATCC 13 880, *Klebsiella pneumoniae* ATCC 10 031 and BC 6, *Proteus Mirabilis* BC 17, *Proteus rettgeri* BC 7, *Enterobacter cloacae* ATCC 13 047, *E. coli* R+TEM(β-lactamase carrier) and *K. pneumoniae* 1088 E (β-lactamase carrier).

Table 1 which follows lists the minimum inhibitory concentrations (MIC) determined for typical representatives of the compounds according to the invention. These are the sodium salts of compounds of the formula I, where A=p-hydroxyphenyl and R is defined as follows:

| Compound | R |
|---|---|
| A | $-NH-\langle\text{phenyl}\rangle-SO_2NH_2$ |
| B | $-NH-\langle\text{phenyl}\rangle-SO_2NH-\langle\text{N=N ring}\rangle$ |
| C | $-NHCH_2-\langle\text{thiophene}\rangle-SO_2NH_2$ |

| Compound | R |
|---|---|
| D | 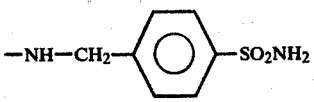 |
| E | Temocillin |

TABLE I

| Compound | E. coli ATCC 11775 | Serr. marc. ATCC 13880 | K. pneum. ATCC 10031 | K. pneum. BC 6 | Prot. mir. BC 17 | Prot. rettg. BC 7 | Eb. cloac. ATCC 13047 | E. coli R+ TEM | K. pneum. 1088 E |
|---|---|---|---|---|---|---|---|---|---|
| A | 1 | 1 | 1 | 1 | 1 | 2 | 1 | 1 | 4 |
| B | 0.25 | 0.5 | 0.25 | 0.25 | 0.06 | 0.25 | 0.12 | 0.25 | 1 |
| C | 1 | 2 | 1 | 1 | 0.12 | 2 | 1 | 2 | 8 |
| D | 2 | 2 | 1 | 1 | 0.5 | 4 | 1 | 2 | 8 |
| E | 4 | 8 | 4 | 2 | 2 | 4 | 4 | 8 | 4 |

In order to demonstrate the particularly good activity of one of the 6α-methoxy-penicillins according to the invention, the activity of compound A in vitro against 20 Serratia marcescens carrying β-lactamase was tested in comparison with Temocillin (Compound E), using the method described:

TABLE II

| Pathogen | Inoculum | Geometric Mean (MIC) [Range (µg/ml)] | |
|---|---|---|---|
| | | A | E |
| Serr. marc. | 5 × 10⁴ | 2.8 [2–8] | 10.2 [8–16] |
| (20) | 5 × 10⁶ | 10.2 [4–32] | 24.3 [16–>64] |

The acute toxicity was determined by oral and subcutaneous administration of the compounds of Tables I and II in increasing doses to white laboratory mice.

The $LD_{50}$ is the dose which results in the death of 50% of the animals within 8 days. All the substances had an $LD_{50}$ of over 4 gm/kg when administered orally and an $LD_{50}$ of over 2 gm/kg when administered subcutaneously, i.e. no animals died at a dose of 2 gm/kg, and the substances are therefore practically non-toxic.

A number of the compounds according to the invention were tested in vivo on experimental infections in mice. E. coli ATCC 11775 were used as the pathogenic bacteria. An intraperitoneal infection was produced with 0.2 ml of a 5% mucin suspension of the bacteria. This corresponds to about $1.4 \times 10^6$ E. coli bacteria per mouse. Female mice of the NMRI strain were divided up into groups of 10 animals, two groups were untreated, the other groups were treated subcutaneously with various doses of the penicillin according to the invention, to determine the $ED_{50}$ (dose at which 50% of the animals survived). One treatment was given (1 hour post infectionem).

In both cases, the observation period was 7 days. The results of these tests with 2 representatives of the penicillins according to the invention, compared with Temocillin, are shown in Table 3 which follows:

TABLE III

| Compound | E. coli infection $ED_{50}$ (mg/kg) |
|---|---|
| A | 4.0 |
| B | 6.1 |
| E | >20 |

A further object of this invention is to provide pharmaceutical compositions which can be used for the treatment of infectious diseases both in humans and in animals.

The preferred pharmaceutical preparations include tablets, coated tablets, capsules, granulates, suppositories, solutions, suspensions, emulsions, ointments, gels, creams, powders and sprays. Advantageously, the active substance or a mixture of the various active substances of the formula I are administered, in human or veterinary medicine, in a dose of between 5 and 500, preferably 10 to 200 mg/kg body weight per 24 hours, possibly in the form of several single doses. A single dose contains the active ingredient or ingredients according to the invention, preferably in amounts of from about 1 to 250, more particularly 10 to 60 mg body weight. However, it may be necessary to deviate from the doses stated above, depending on the nature and body weight of the patient being treated, the nature and gravity of the disease, the type of preparation and the method of administration of the pharmaceutical product and also the period or interval within which the product is administered.

Thus, in some cases it may be adequate to use less than the above-mentioned quantity of active substance, whereas in other cases it may be necessary to use more than the amount of active ingredient specified above. The optimum dose and method of administration of the active ingredients required in each case can readily be determined by anyone skilled in the art from his specialized knowledge.

When used as a feed additive, the new compounds may be administered in the usual concentrations and preparations together with the feed or with feed preparations or with drinking water. They can thereby prevent, remedy and/or cure infections caused by gram-negative and gram-positive bacteria and can also promote growth and bring about an improvement in the utilization of the feed.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.71 to 11.42 mgm/kg body weight, preferably 2.85 to 7.14 mgm/kg body weight. The daily dose is from 2.14 to 35.71 mgm/kg, preferably 8.57 to 21.42 mgm/kg.

The following examples illustrate a few pharmaceutical compositions comprising a compound of the present invention as an active ingredient and represent the best modes contemplated of using the invention.

EXAMPLE 23

Tablets containing
6β-{D-α-[3-(4-hydroxy-2-p-sulfamoylanilino-5-pyrimidinyl]-ureidol-benzylamido}-6α-methoxy-penicillanic acid sodium salt A mixture consisting of 2 kg of active ingredient, 5 kg of lactose, 1.8 kg of potato starch, 0.1 kg of magnesium stearate and 0.1 kg of talcum is compressed in the usual way to form tablets, each containing 200 mg of active ingredient.

EXAMPLE 24

Coated tablets containing
6β-{D-α-[3-(4-hydroxy-2-p-sulfamoylanilino-5-pyrimidinyl)-ureido]-benzylamido}-6α-methoxy-penicillanic acid sodium salt Compressed tablets are produced analogous to Example 23, which are then coated in the usual way with a thin shell consisting of a mixture of sugar, potato starch, talcum and tragacanth.

EXAMPLE 25

Capsules containing
6β-{D-α-[3-(4-hydroxy-2-p-sulfamoylanilino-5-pyrimidinyl)-ureido]-benzylamido}-6α-methoxy-penicillanic acid sodium salt 5 kg of active ingredient are filled into hard gelatin capsules in the usual way, each capsule containing 500 mg of the active ingredient.

EXAMPLE IV

Dry ampules containing
6β-{D-α-[3-(4-hydroxy-2-p-sulfamoylanilino-5-pyrimidinyl)-ureido]-benzylamido}-6α-methoxy-penicillanic acid sodium salt Under aseptic conditions, 251 gm of active substance were dissolved in 2008 ml of distilled water for injection. The solution was filtered through a Millipore filter (pore size 0.22 μm, product of the Millipore Corporation, Bedford, Mass.). 2.0 ml amounts of the solution were poured into 1000 vials (capacity 10 ml) and lyophilisation was carried out. The vials were then sealed with a rubber stopper and an aluminum cover. In this way, vials (No. A) were obtained, each containing 250 mg of active ingredient.

A physiological saline solution for injection was poured into ampules in amounts of 2.0 ml, and the ampules were sealed. In this way, ampules (No. B) were obtained. The physiological saline solution in the ampule (No. B) was poured into the vials (No. A), thus producing an injectable solution suitable for intravenous administration.

Distilled water for injection was poured into the vials (No. A) in amounts of 20 ml, and the solution was dissolved in a 5% solution of glucose for injections (250 ml). In this way, solutions for continuous infusion were prepared.

Any one of the other compounds embraced by formula I or a non-toxic, pharmacologically acceptable salt thereof may be substituted for the particular active ingredient in Examples 23 through 25. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula wherein

A is phenyl, p-hydroxy-phenyl, 2-thienyl or 3-thienyl; and

R is cyclopropyl, —NH—$R_1$, $R_1$ is straight or branched aliphatic hydrocarbyl of 1 to 4 carbon atoms; straight or branched aliphatic hydrocarbyl of 2 to 4 carbon atoms hydroxy-substituted in 2-, 3- or 4-position; cycloalkyl of 3 to 6 carbon atoms; hydroxy-cycloalkyl of 3 to 6 carbon atoms; unsubstituted or monosubstituted 3-pyridyl, where the substituent is hydroxyl, methylsulfinyl, methylsulfonyl or aminosulfonyl; unsubstituted or monosubstituted 2-furylmethyl, where the substituent is hydroxyl, methylsulfinyl, methylsulfonyl or aminosulfonyl; unsubstituted or monosubstituted 2-thiazolylmethyl, where the substituent is hydroxyl, methylsulfinyl, methylsulfonyl or aminosulfonyl; unsubstituted or monosubstituted 2-thienylmethyl, where the substituent is hydroxyl, methylsulfinyl, methylsulfonyl or aminosulfonyl; unsubstituted or monosubstituted 3-imidazolylmethyl, where the substituent is hydroxyl, methylsulfinyl, methylsulfonyl or aminosulfonyl; or unsubstituted or monosubstituted 3-pyridylmethyl, where the substituent is hydroxyl, methylsulfinyl, methylsulfonyl or aminosulfonyl;

n is 0 or 1;

$R_2$ and $R_3$ which may be identical to or different from each other are each hydrogen, hydroxyl, acetylamino, aminocarbonylamino, nitro, aminocarbonyl, cyano, methylsulfinyl, methylsulfonyl, aminosulfonyl, methylaminosulfonyl, aminocarbonyl-methyleneaminosulfonyl, 2'-hydroxyethyl-aminosulfonyl, cyano-aminosulfonyl, aminocarbonyl-aminosulfonyl, acetyl-aminosulfonyl, methylsulfonyl-aminosulfonyl or acetylhydrazinosulfonyl; and m is 2, 3 or 4;

or a non-toxic, pharmacologically acceptable salt thereof formed with an inorganic or organic base.

2. A compound of claim 1 where

A has the meanings defined in claim 1, and

R is p-aminosulfonylanilino, p-methylsulfinylanilino, p-methylsufonylanilino, m-hydroxy-p-aminosulfonylanilino, p-aminocarbonylmethyleneaminosulfonylanilino, p-(4',5'-dihydro-imidazol-2'-yl)-aminosulfonylanilino, p-(3',4',5',6'-tetrahydropyrimidin-2'-yl)-aminosulfonylanilino, p-(4',5',6',7'-tetrahydro-1,3-diazepin-2'-yl)-aminosulfonylanilino, p-(4',5'-dihydro-thiazol-2'-yl)-aminosulfonylanilino, p-hydroxybenzylamino, p-aminosulfonylbenzylamino, isopropylamino, 4'-hydroxy-cyclohexylamino, 5'-aminosulfonyl-2'-thienylmethylamino, 2'-furylmethylamino, 3'-pyridyl-methylamino or 4'-hydroxy-3'-pyridylamino, or a non-toxic, pharmacologically acceptable salt thereof formed with an inorganic or organic base.

3. A compound of claim 1 which has the D=R-configuration.

4. A compound of claim 1, which is 6β-{D-α-[3-(4-hydroxy-2-p-(4',5',6',7'-tetrahydro-1,3-diazepin-2'-yl)-aminosulfonylanilino-5-pyrimidinyl)-ureido}-p-hydroxy-benzylamido}-6α-methoxy-penicillanic acid or the sodium salt thereof.

5. A compound of claim 1, which is 6β-{D-α-[3-(4-hydroxy-2-p-sulfamoylanilino-5-pyrimidinyl)-ureido]-p-hydroxybenzylamido}-6α-methoxy-penicillanic acid or the sodium salt thereof.

6. An antibacterial pharmaceutical composition consisting essentially of an inert pharmaceutical carrier and an effective antibacterial amount of a compound of claim 1.

7. The method of inhibiting the growth of or destroying pathogenic bacteria in a warm-blooded animal in need thereof, which comprises perorally, parenterally, rectally or topically administering to said animal an effective antibacterial amount of a compound of claim 1.

* * * * *